United States Patent [19]
Häberlein et al.

[11] Patent Number: 5,550,468
[45] Date of Patent: Aug. 27, 1996

[54] METHOD AND APPARATUS FOR ADJUSTING THE OPERATING DIAMETER OF A PROBE IN A ROTATING TESTING HEAD

[75] Inventors: Peter Häberlein; Hans Link, both of Reutlingen, Germany

[73] Assignee: Institut Dr. Friedrich Forster Prufgeratebau GmbH & Co. KG, Reutlingen, Germany

[21] Appl. No.: 216,681

[22] Filed: Mar. 23, 1994

[30] Foreign Application Priority Data

Apr. 30, 1993 [DE] Germany ................ 43 14 274.5

[51] Int. Cl.⁶ .................. G01N 37/00; G01N 27/72; G01R 33/12
[52] U.S. Cl. .................. 324/225; 324/238; 324/262
[58] Field of Search .................. 324/225, 226, 324/227, 262, 234, 237, 238, 240, 242, 243

[56] References Cited

U.S. PATENT DOCUMENTS

| | | |
|---|---|---|
| 3,612,987 | 4/1970 | Placke et al. . |
| 4,554,496 | 11/1985 | Rudiche, Jr. et al. . |
| 4,596,953 | 6/1986 | Nagasaka et al. .......... 324/262 |
| 4,641,532 | 2/1987 | Rohrer . |
| 5,023,550 | 6/1991 | Yamazaki et al. .......... 324/242 |
| 5,187,435 | 2/1993 | Geweke . |

FOREIGN PATENT DOCUMENTS

| | | |
|---|---|---|
| 0398002 | 11/1990 | European Pat. Off. . |
| 7038526 | 10/1970 | Germany . |
| 2847716 | 5/1980 | Germany . |
| 2936660 | 3/1981 | Germany . |
| 3324444 | 1/1984 | Germany . |
| 3603153 | 8/1987 | Germany . |
| 3739190 | 6/1989 | Germany . |
| 9010086 U | 11/1990 | Germany . |
| 3937261 | 5/1991 | Germany . |
| 4021546 | 1/1992 | Germany . |
| 4141257 | 6/1993 | Germany . |
| 681181 | 1/1993 | Switzerland . |
| 2197070 | 5/1988 | United Kingdom . |
| 2045436 | 10/1990 | United Kingdom . |

OTHER PUBLICATIONS

"Messwertgeber zur analogen and digitalen Winkel– und Wegmessung", TWK Information 14/85, pp. 6 & 7 (no translation).

*Primary Examiner*—Walter E. Snow
*Attorney, Agent, or Firm*—Bell, Seltzer, Park & Gibson, P.A.

[57] ABSTRACT

A method and apparatus for testing an elongate product for faults and defects, which comprises a rotatable testing head which permits the elongate product to be passed coaxially therethrough and which mounts a pair of testing probes so as to permit adjustment of their operating diameter. In order to automatically adjust the positions of the probes to accommodate elongate products of different sizes, there is provided an external adjustment unit, which stops the testing head in a predetermined angular position. The adjustment unit contains an external adjustment drive and when the rotation of the testing head has stopped, the external adjustment drive is advanced into operative engagement with the adjustable mounting of the testing probes. A measuring pin is also advanced into contact with the mounting of the testing probes so as to monitor the exact position of the probes, and during the repositioning of the probes a signal from the measuring pin is fed back to a control device to assure the precise positioning of the probes.

18 Claims, 1 Drawing Sheet

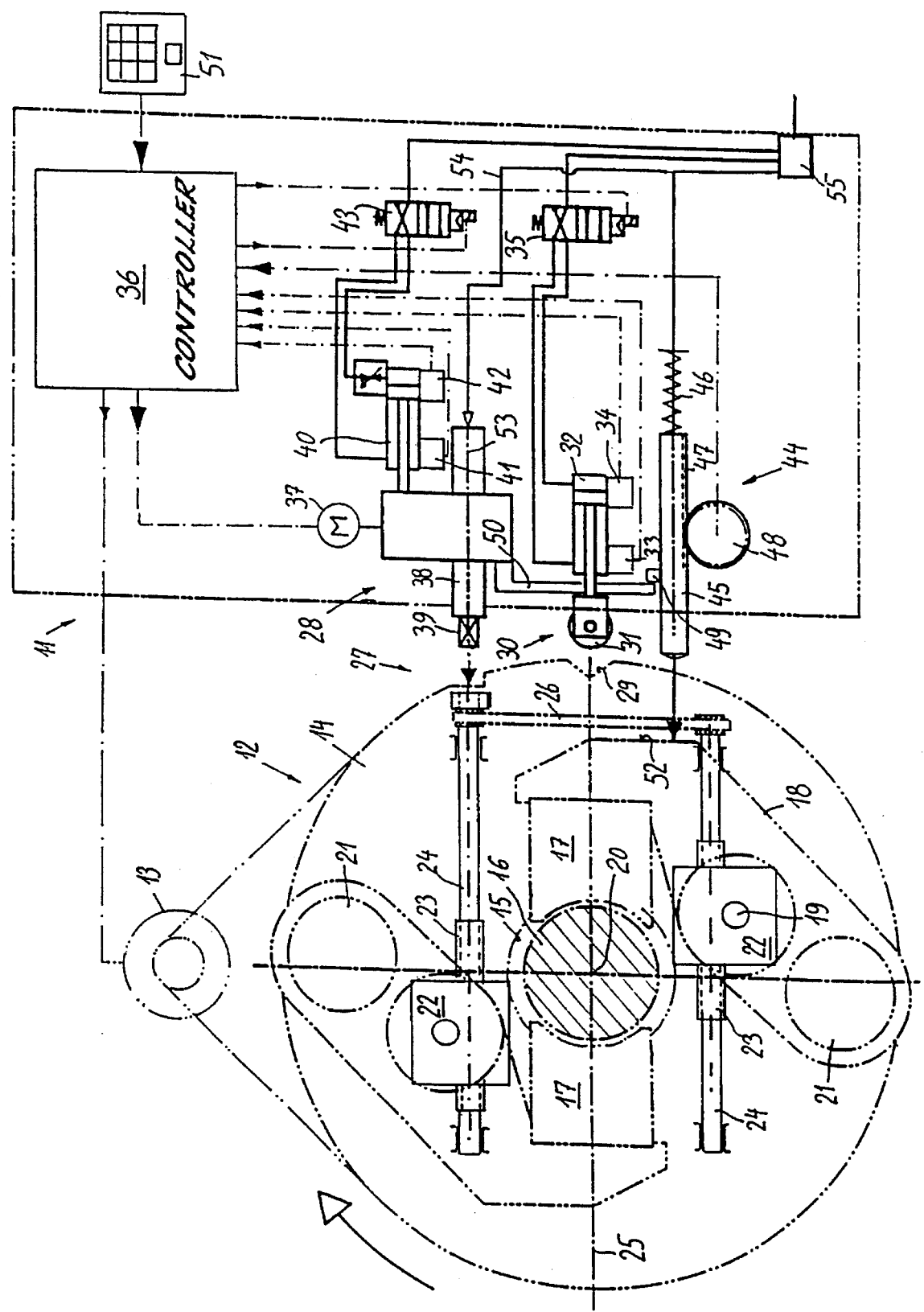

METHOD AND APPARATUS FOR ADJUSTING THE OPERATING DIAMETER OF A PROBE IN A ROTATING TESTING HEAD

BACKGROUND OF THE INVENTION

The invention relates to a method and a device for diameter adjustment for a probe for measuring and/or testing devices provided on a test head driven in rotary manner, e.g. according to the stray flux measurement principle.

In the case of such measuring and/or testing devices the distance between the probe and the testpiece, e.g. a wire or a rod, is particularly important, because the quality of the measurement or test result is dependent thereon. In the case of stray flux testing equipment, in which a magnetic yoke subject to a high frequency induces a stray flux in the surface of the test material and the exit of a deflected stray flux is measured at fault or defect points, use is even made of rubbing or abrading probes on the test material surface. Their spacing must therefore be adjusted in accordance with the test material dimensions.

A manual adjustment has already been proposed for this purpose. In this case an adjustment can take place with a spanner using a scale and with the test head stationary.

The problem of the invention is to simplify the adaptation of a testing device to different circumstances, particularly different testpiece dimensions and in particular reduce the need for manual action.

SUMMARY OF THE INVENTION

The above and other objects and advantages of the present invention are achieved by the provision of a method and apparatus for inspecting an elongate product for faults and defects, and which comprises a testing head which is mounted for rotation about a predetermined axis, and drive means for rotating the testing head about the predetermined axis. At least one testing probe is mounted to the testing head so as to permit adjustment of the operating diameter of the testing probe, and the mounting means includes first coupling means. An external adjustment drive is positioned adjacent the testing head, with the external adjustment drive having second coupling means. An indexing means is provided for stopping and holding the testing head in a predetermined circumferential position, in which the first and second coupling means are juxtaposed to each other, and a coupling drive means is provided for operationally coupling the first and second coupling means in the predetermined circumferential position. Thus the external adjustment drive is operationally connected to the diameter adjustment means for adjusting the operating diameter of the probe.

Thus, the testing head is fixed in an adjustment position, particularly after previously being switched down from its normal speed of e.g. 1500 r.p.m. or higher to a creep feed. In this adjustment position an external adjustment drive, e.g. a polygonal shaft, can be coupled to a corresponding coupling point of the testing head and the adjustment can be made. An indexing member, e.g. a roll, keeps the testing head in the adjustment position in the meantime.

To achieve a reliable positioning of the probe in the desired position, not only are there setting means, on which it is possible to e.g. set a new desired diameter by a manual input, measurement of the product to be tested or the giving of a program, but also through the measuring means the actual position of the probe is measured directly or by means of parts firmly connected thereto, e.g. the testing levers, in the testing head and the measurement result is utilized for the control of the adjustment drive.

The indexing, the adjustment drive with the associated coupling half and the measuring means are preferably provided in a single unit, which can also contain an advance drive, which advances the said devices following indexing against the testing head.

The measuring means can comprise a measuring pin, which e.g. by means of a rack drives an angle coder, which converts the measurement result into electrical signals. To ensure that the measurement and/or coupling also in the case of testing devices operating in a dirty environment can bring about a completely satisfactory and reliable adjustment, prior to the resetting the reference or coupling faces can be cleaned. This can in particular take place by blowing off by means of compressed air ducts, which can be made in the measuring pin or coupling spindle. As preferably the advance drive or the movement of the indexing member are brought about by a pneumatic drive, compressed air is already available at the adjustment unit.

As a result of the diameter adjustment according to the invention an activity which has previously been performed manually can be automated in a simple and reliable manner. Within the framework of an automatic production sequence certain diameter changes can already be preprogrammed. It would also be possible to link the adjustment of the testing head with corresponding adjustments on the production machine, which generally follows the testing device. Thus, not only is time saved and the adjustment performed with maximum accuracy, i.e. leading to considerable advantages with respect to the reliability of the measurement and test result, but also possible errors and damage due to unreliable or omitted adjustment of the probe in the testing head are avoided. The term probes here covers all devices which are in a specific spatial relationship with the object to be measured or tested and not only for receiving measurement or test signals, but also for delivering signals, electrical or magnetic fields or other physical quantities used for measurement or testing purposes.

These and further features and developments of the invention can be gathered from the claims, description and drawings and the individual features, both singly and in the form of subcombinations, can be realized in an embodiment of the invention and in other fields and can represent advantageous, independently patentable constructions for which protection is hereby claimed. An embodiment of the invention is described in greater detail hereinafter relative to the drawings.

DESCRIPTION OF THE EMBODIMENT

The single drawing is a diagrammatic representation of a measuring and testing device with diameter adjustment.

The drawing shows a diameter adjusting device 11 for a testing head 12, which is rotated by a diagrammatically indicated drive 13 and forms part of a testing device, which is located in a material testing and/or machining line. Such rotating testing heads can be used for inspecting for faults and defects wires, pipes, rods, etc., e.g. for cracks, inclusions, etc. Numerous different testing methods could be used, e.g. the eddy current method, the steady field stray flux method or the like, including ultrasonic methods. Apart from fault testing, it is also possible to carry out continuous thickness measurements and the like using such testing heads.

In the represented embodiment the testing head 12 contains a rotating disk 14 with a central opening 15 through which passes the object 16, e.g. a metal rod, to be tested or inspected. It normally comes directly from a manufacturing plant and is tested for faults immediately following its manufacture. Testing takes place by two facing probes 17, which are fitted to testing levers 18. In the drawing the probes 17 are shown in the form of jaws or shoes, but can have completely different constructions as a function of the particular testing or measuring method. They could e.g. in each case contain two lateral poles of a magnet yoke and with a sensor between them and which is movable, e.g. spring-mounted with respect to the said poles and in certain measuring methods, e.g. the stray flux method, can also rub on the surface of the object 16.

The testing lever 18 is pivotable about a shaft 19 parallel to the conveying direction of the object 16 or the rotation shaft 20 of the testing head. Each of the two testing levers 18 is so balanced by a counterweight 21, that on rotating the testing head, which can take place at a speed of up to 2000 r.p.m. and higher as a function of the head diameter, the testing levers can move substantially uninfluenced by centrifugal forces.

The shafts 19 are fitted to slides 22, which can be displaced by means of a threaded spindle 23. Each of the two threaded spindles 23 is fitted to a shaft 24, which are mounted parallel to one another in the chord direction, namely parallel to a radial plane 25, which passes centrally through the probe.

Both the shafts 24 are coupled with one another for synchronous movement namely by a toothed belt drive 26. As the threaded spindles and the associated internal thread in the slide 22 have different thread pitch directions on the two sides, in the case of a synchronous rotation of the two shafts 24, the slides move in opposite directions to one another.

The levers are pivotably articulated by means of shafts 19 to the slide, but are so stop-limited, that at each position of the slide 22 the probe 17 assumes a fixed minimum spacing with respect to the rotation shaft 20. It can give way outwards with respect to a spring tension or other forces, such as e.g. residual centrifugal forces.

The testing head 12 has a coupling means 27 for coupling an external adjustment drive 28, which can be constructed as an internal polygon at the end of one of the shafts 24.

The coupling means 27 provided in the vicinity of the outer circumference of the disk 14 has a given circumferential spacing with respect to an indexing notch 29 of the disk belonging to the indexing means 30. There is also a roll 31, which is provided on the stationary adjustment unit 11 and can be adjusted into and out of engagement with the indexing notch 29 by means of a pneumatic cylinder 32. The switches 33, 34 are operated on reaching the two operating transmitting positions of the indexing means. A pneumatic valve 35, controlled by an electronic control device 36, brings about the pneumatic action on the cylinder 32.

The adjustment drive 28 has an adjustment shaft 38 rotatable by a motor, e.g. an electric stepping or geared motor or some similar very precisely controllable drive, which has at its end associated with the testing head a polygon 39 as coupling means. The adjustment shaft is displaceable by means of a pneumatic cylinder 40 in the longitudinal direction, i.e. towards and away from the testing head.

Here again switches 41, 42 monitor the reaching of the two end positions of the adjustment drive 28. Therefore the two pneumatic cylinders 32, 40 form a displacement drive for the indexing means 30 and the adjustment drive 28. The pneumatic cylinder 40 is controlled by the control device 36 by means of a pneumatic valve 43.

The adjustment unit 11 also contains measuring means 44 with a measuring pin 45, which under the tension of a spring 46 is displaceable in the direction of the testing head 12. During this displacement the measuring pin 45 moves, by means of a rack 47 located thereon, an absolute angle coder 48 serving as an electric signal generator and whose signals are supplied to the control device 36.

For its movement towards the testing head the measuring pin 45 could also be located on a movable slide. However, preferably, it is connected by means of a stop 49 and a corresponding stop lever 50 to the advance drive of the adjustment drive 28 and is brought into the inoperative position counter to the tension of the spring 46 if the pneumatic cylinder 40 is in the represented position, in which the adjustment drive is disengaged.

The control device 36 can be constructed in the conventional manner as an electric or electronic control device and can be constructed for processing signals from a setting unit 51, e.g. an input unit with a keyboard, measuring signals from the angle coder 48 and different switch signals and can generate output signals for controlling the valves 35, 43, as well as the adjustment drive motor 37.

Function

On operating the testing device the testing head 12 is rotated by the testing head drive 13 and therefore rotates the probe 17 around the object 16 or testpiece running in the longitudinal direction and at right angles to the drawing plane. The testing levers 18 are set in such a way that a predetermined constant minimum spacing between the probe and the object is maintained or a sensor is guided with a predetermined force in rubbing manner on the surface of the testpiece 16.

If the setting is changed as a result of a change in the diameter of the testpiece 16, there must also be an adjustment of the reciprocal spacing of the probe 17, so that the predetermined, optimum spacing again exists. This takes place in that a new desired value for the probe spacing or the new testpiece diameter is inputted at the setting device 51. Alternatively these values could also be taken over by diameter measurements of the testpiece or from operating programs.

Following the start signal for the adjustment the control device 36 supplies a pulse to the testing head drive, which reduces it to the creep speed. If e.g. the testing head operates at 1500 r.p.m. the drive can now be reduced to a speed of e.g. 20 to 50 r.p.m. As the testing head drive takes place by means of a frequency changer, this can be brought about by a corresponding influencing of the latter. It is also possible to firstly completely stop the testing head and then to start it up again at the creep speed.

The control device then acts on the solenoid valve 35, which by means of the cylinder 32 advances the indexing member constructed as a roll 31 against the disk 14, where the roll rolls until it drops into the indexing notch 29. As a result the switch 33 is operated and by means of the control device 36 leads to an immediate stoppage of the testing head drive. The roll remains engaged in the notch 29, so that now the testing head is mechanically locked in the indexing position.

By means of the valve 43 the pneumatic cylinder 40 is then actuated and advances the adjustment drive 28 against the testing head. In the indexing position the connection hexagonal recess of the coupling means 27 is positioned in alignment with the adjustment shaft, so that the countercoupling member formed by the polygon 39 on the adjustment shaft 38 is locked therein.

Simultaneously the stop lever 50 is moved forwards, so that the measuring pin 45 can also move forwards under the tension of the spring 46 and rests on a reference surface 52 on one of the two levers 18.

As shown in the drawing, prior to coupling in and prior to the engagement of the measuring pin 45, an air blast channel 53 passing along the adjustment axis and the measuring pin and which is supplied by air blast lines 54 from the common pneumatic connection 55, blows out air for cleaning the coupling and the reference surface 52.

The switch 41 indicates the coupling of the adjustment drive to the testing head. The motor of the adjustment drive 28 is started from the control device, so that the shafts 24 are rotated and consequently the slides 22 are moved in opposition in the direction of the new probe position.

The measuring pin 45 resting on a reference surface of a testing lever 18, by means of its transducer 48 supplies the actual value of the lever and therefore the probe to the control device, which compares the actual value with the desired value inputted by means of the setting device 51 and switches off the adjustment drive 28 if the actual value corresponds to the desired value. As a result of the synchronous movement of the two shafts (synchronized by means of the toothed belt 26), it is only necessary to perform the measurement on one of the testing levers 18.

Then the control device supplies the signal for ending the setting and the pneumatic cylinders 32,40 retract the adjustment drive 28 and the indexing means 30. This is indicated back to the control device by means of the switches 34,42. The measuring pin 45 follows the return of the adjustment drive, because the stop arm 50 returns it counter to the tension of the spring 46. Thus, the setting process is at an end and the testing head can be rotated again for continuing testing.

Thus, the invention describes a fully automatic method and a system making it possible to accurately adjust the probe of a rotating measurement or testing head under the control of the particular actual dimension.

We claim:

1. An apparatus for inspecting an elongate product for faults and defects, and comprising
   a testing head which is mounted for rotation about a predetermined axis,
   drive means for rotating the testing head about said predetermined axis,
   at least one testing probe,
   means mounting said one testing probe to said testing head so as to permit adjustment of the operating diameter of said one testing probe, said mounting means including first coupling means,
   an external adjustment drive positioned adjacent the testing head, the external adjustment drive having second coupling means,
   indexing means for stopping and holding the testing head in a predetermined circumferential position, in which the first and second coupling means are juxtaposed to each other,
   coupling drive means for operationally coupling said first and second coupling means when said testing head is in said predetermined circumferential position,
   whereby said external adjustment drive is operationally connected to said diameter adjustment means for adjusting the operating diameter of said at least one probe.

2. An inspecting apparatus according to claim 1, further comprising:
   external measuring means for measuring the probe position, and means for bringing the external measuring means into a measuring position engaging the testing head when it is stopped in the predetermined circumferential position, and
   control means for controlling the external adjustment drive and which is operable as a function of a desired diameter setting means and the output of the external measuring means.

3. An inspecting apparatus according to claim 1, wherein the at least one probe is an electro-magnetic testing probe.

4. An inspecting apparatus according to claim 1, wherein the indexing means includes an indexing member which is movable into an indexing position and which cooperates with an indexing mark on the testing head and initiates an indexing signal which stops the testing head drive.

5. An inspecting apparatus according to claim 4, wherein the indexing mark is a notch on the testing head.

6. An inspecting apparatus according to claim 5, wherein the indexing member includes a roller for engaging said notch.

7. An inspecting apparatus according to claim 1, wherein the testing head drive means includes speed reduction means which is operable prior to actuation of the indexing means.

8. An inspecting apparatus according to claim 1, wherein the coupling drive means is provided on an adjustment shaft rotatable for adjustment purposes and which for coupling purposes can be moved by means of an advance drive towards the testing head.

9. An inspecting apparatus according to claim 2, wherein the measuring means includes a measuring member movable by means of an advance drive into measuring engagement with the testing head.

10. An inspecting apparatus according to claim 9, wherein the measuring member is positioned to contact a testing lever which carries said one probe.

11. An inspecting apparatus according to claim 10, wherein the measuring member is a spring-loaded measuring pin.

12. An inspecting apparatus according to claim 11, wherein the measuring member is drivingly connected to a rotary measurement transducer.

13. An inspecting apparatus according to claim 12, wherein the measurement transducer is an absolute angle encoder.

14. An inspecting apparatus according to claim 2, wherein the adjustment drive, indexing means, coupling drive means and measuring means are mounted on an external adjustment unit.

15. An inspecting apparatus according to claim 1, wherein the coupling drive means includes cleaning means adapted for coming into operation prior to said coupling action.

16. An inspecting apparatus according to claim 9, wherein the measuring member includes cleaning means adapted for coming into operation prior to said engagement with the testing head.

17. An inspecting apparatus according to claim 15, wherein the cleaning means comprises at least one air blast channel penetrating said coupling means.

18. An inspecting apparatus according to claim 16, wherein the cleaning means comprises at least one air blast channel penetrating said measuring member.

* * * * *